(12) United States Patent
Brommersma

(10) Patent No.: US 8,265,727 B2
(45) Date of Patent: Sep. 11, 2012

(54) SURGICAL VAPORIZATION ELECTRODE WITH AN ELECTRODE HEAD

(75) Inventor: Pieter Brommersma, Bargteheide (DE)

(73) Assignee: Olympus Winter & IBE GmbH, Hamburg (DE)

( * ) Notice: Subject to any disclaimer, the term of this patent is extended or adjusted under 35 U.S.C. 154(b) by 473 days.

(21) Appl. No.: 12/267,982

(22) Filed: Nov. 10, 2008

(65) Prior Publication Data

US 2009/0125021 A1 May 14, 2009

(30) Foreign Application Priority Data

Nov. 13, 2007 (DE) .................. 10 2007 054 438

(51) Int. Cl.
*A61B 5/04* (2006.01)

(52) U.S. Cl. .................. 600/372; 600/373; 600/394

(58) Field of Classification Search .......... 600/372–382, 600/394, 395; 606/41, 47, 129; 607/21
See application file for complete search history.

(56) References Cited

U.S. PATENT DOCUMENTS

| 4,254,356 | A | * | 3/1981 | Karikas .................. 313/623 |
| 5,403,311 | A | * | 4/1995 | Abele et al. .............. 606/49 |
| 5,480,398 | A | * | 1/1996 | Eggers .................... 606/29 |
| 5,944,715 | A | * | 8/1999 | Goble et al. .............. 606/41 |
| 6,210,405 | B1 | * | 4/2001 | Goble et al. .............. 606/41 |
| 6,238,347 | B1 | * | 5/2001 | Nix et al. ................ 600/463 |
| 6,332,881 | B1 | * | 12/2001 | Carner et al. ............ 606/41 |
| 2005/0119650 | A1 | * | 6/2005 | Sanders et al. ........... 606/41 |
| 2005/0277915 | A1 | * | 12/2005 | DeCesare et al. ......... 606/41 |
| 2005/0288665 | A1 | * | 12/2005 | Woloszko ................ 606/41 |
| 2007/0179497 | A1 | * | 8/2007 | Eggers et al. ............ 606/41 |
| 2008/0077129 | A1 | | 3/2008 | Van Wyk et al. |

FOREIGN PATENT DOCUMENTS

DE 295 21 027 U1 10/1996
EP 1 457 162 A1 9/2004

* cited by examiner

*Primary Examiner* — Nicholas Lucchesi
*Assistant Examiner* — Gerald Landry, II
(74) *Attorney, Agent, or Firm* — Rankin, Hill & Clark LLP

(57) ABSTRACT

A surgical vaporization electrode (1) including an electrode head (2) which in turn is fitted with a functional surface (6) and which is connected at a minimum of one connection site (10) to a feed conductor (3) enclosed by an insulating sheath (4), is characterized in that the surface zone (7) of the electrode head (2) surrounding the connection site (10) is fitted with a ceramic covering (8).

15 Claims, 1 Drawing Sheet

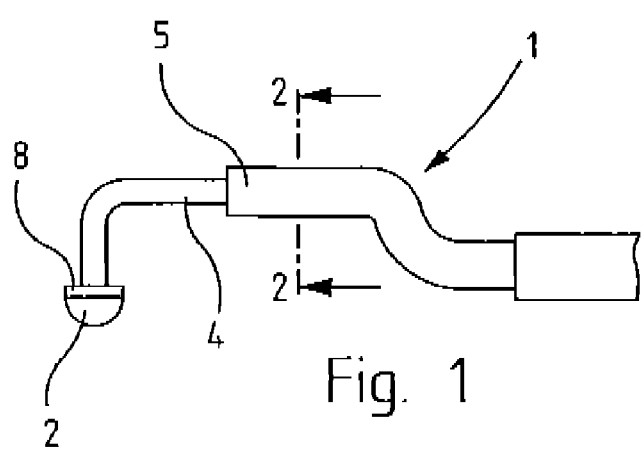
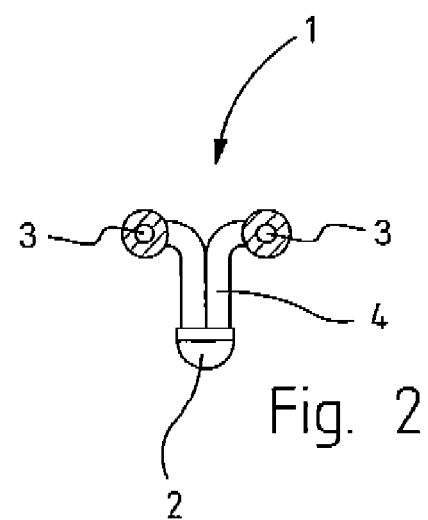
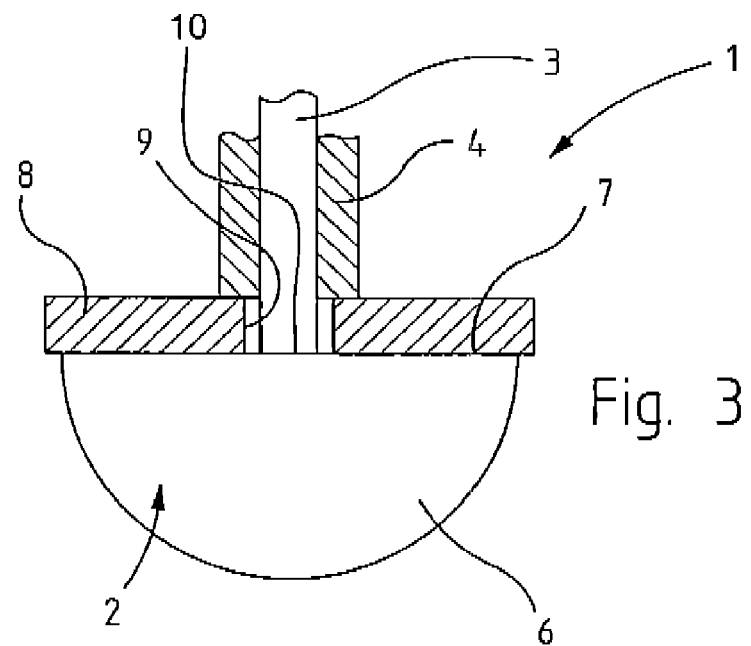

SURGICAL VAPORIZATION ELECTRODE WITH AN ELECTRODE HEAD

BACKGROUND OF THE INVENTION

1. Field of the Invention

The present invention relates to a vaporization electrode.

2. Description of Related Art

Electrodes of the kind illustratively disclosed in DE 295 21 028 U1 are used for vaporization in the presence of water, for instance in the bladder. The functional surface of the electrode is moved against a tissue surface. The high frequency (hf) of the electrode causes the tissue to heat to carbonization.

In earlier techniques, when working in a poor electrically conducting liquid, the hf current loading the electrode was constrained, upon its making contact with the tissue, to pass through latter until reaching an external neutral electrode. The tissue was heated by the current.

More modern techniques are carried out in liquids that conduct electricity well. The current from the vaporization electrode's functional surface passes through the liquid to a nearby return electrode. The tissue is heated by a plasma building up above the functional surface.

However, problems are incurred because the plasma may be formed at all electrically conducting vaporization electrode areas. In other words, the plasma is formed not only at the functional surface, but also elsewhere. Therefore, the feed wire is protected by an insulating sheath to preclude spurious plasma formation.

On the other hand, the insulating sheath is delicate. Because of its complex assembly, it is made at least of plastic in the feed conductor's end zone near the electrode. However, this plastic is thermally susceptible. Plasma forming in the vicinity of the insulating sheath destroys it.

Accordingly, the objective of the present invention is to preclude destruction by plasma of a vaporization electrode of the above cited kind.

BRIEF SUMMARY OF THE INVENTION

In the present invention, the electrode head's surface zone surrounding the feed conductor's connection site is fitted with a ceramic covering. The ceramic covering precludes plasma formation at the electrode head's covered surface zones. In other words, the ceramic covering precludes plasma formation in the vicinity of the feed conductor's connection site. This feature protects the susceptible insulating sheath and precludes deleterious destruction that might render useless the entire vaporization electrode. Where several feed conductors are connected to one electrode head, they must be appropriately fitted with appropriate separate ceramic coverings or a single common one.

In this respect, it is advantageous for a vaporization electrode to have an electrode head that includes a convex functional surface and a planar back side on which is configured the connection site, with the back side being covered by a ceramic pane. In this embodiment mode, in which the electrode head comprises a convex functional surface, the electrode head illustratively may be mushroom-shaped or planar. Its flat back side receiving the connection site may be covered by a planar ceramic pane of simple manufacture which precludes plasma formation at its location.

In another embodiment mode, the feed conductor passes through a borehole in the ceramic covering. Its insulating sheath may terminate at that site and is exceptionally well protected against plasma formation. Where the electrode head is connected to several feed conductors, a common ceramic covering fitted with several holes may be used.

The present invention is shown illustratively and schematically in the appended drawings.

BRIEF DESCRIPTION OF THE DRAWINGS

FIG. 1 is a side view of the distal end of a vaporization electrode,

FIG. 2 is a section along line 2-2 of FIG. 1, and

FIG. 3 is an enlarged cutaway in the zone of the electrode head of FIG. 1.

DETAILED DESCRIPTION OF THE INVENTION

The Figures show a surgical vaporization electrode 1 with an electrode head 2 made of an appropriate high-temperature resistant metal. A voltage is applied by a feed conductor 3 to the electrode head 2, said conductor being fitted in the end zone near the electrode head 2 with an insulating, plastic sheath 4. As shown by FIG. 3, the feed conductor 3 is connected to a terminal site 10 at the electrode head 2, for instance by being soldered or welded to it.

In the embodiment mode of FIGS. 1 through 3, the electrode head 2 assumes the shape of a mushroom-electrode with a strongly convex functional surface 6. Its back side 7 is planar and covered by a ceramic pane 8 which is crossed by the feed conductor 3 passing through a borehole 9.

Accordingly, the ceramic pane 8 encloses the connection site 10 of the feed conductor 3 and in this region protects the insulating sheath 4 enclosing the feed conductor 3, because plasma formation is precluded on the back side 7 by the covering ceramic pane 8.

As shown in the embodiment mode of FIG. 1, the feed conductor 3, together with its insulating sheath 4, is substantially bent in the end zone near the electrode head 2. Away from the electrode head 2, the feed conductor 3, together with its insulating sheath 4, runs in the proximal direction into a protective tube 5 and continues in an appropriate shape. Details of such conventional designs illustratively are disclosed in the above cited DE 295 21 028 U1.

As shown in FIG. 2, the single electrode head 2 is connected to two feed conductors 3, each fitted with an insulating sheath 4 and each running in a protective tube 5. This feature, however, is based solely on mechanical grounds. The two feed conductors are connected to the same voltage source. A single feed conductor 3 would suffice.

For manufacturing considerations, and in particular for the ease of assembly, the insulating sheath 4 must be made of plastic, in particular in the end zone of the feed conductor 3 between the protective tube 5 and the electrode head 2. This plastic, however, is susceptible to degradation at very high temperatures.

The vaporization electrode 1 of the present indention is employed in electrically conducting liquids, for instance in bladder prostate resection while using salt-enriched flushing water. The electric current passes from the electrode head 2 and through the ambient flushing water to a nearby neutral electrode configured in said flushing water. As a result, an extremely hot plasma forms above the very convex functional surface 6 of a mushroom-like electrode of the electrode head 2. The plasma is capable of very effectively carbonizing tissue while also destructively affecting other objects such as the plastic of the insulating sheath 4. Unless protected as disclosed herein, after an initial and modest destruction of the insulating sheath 4 in the vicinity of the electrode head, a plasma shall quickly form there too, which will quickly destroy the entire remnant of the insulating sheath 4. Electrical constraints and personal safety then rule out further use of the vaporization electrode 1.

As shown in particular in FIG. 3, the functional surface 6 of the electrode head 2 is unencumbered in the present invention, but the remaining surfaces of the electrode head 2—i.e., the surfaces not used for surgery—are covered by the ceramic pane 8 so that plasma formation is precluded at such surfaces. In other words, plasma formation is precluded especially in the region of the insulating sheath 4.

In the shown embodiment mode fitted with two feed conductors 3, the ceramic pane 8 is fitted with two boreholes 9 and, in an anti-plasma protecting manner, encloses both feed conductors 3 together with their particular insulating sheaths 4.

An electrode suitable for vaporization, other than the above shown button electrode with a convex functional surface 6, may also be used. For instance, the functional surface can be planar.

The back side 7 of a mushroom-like electrode 2 of the shown embodiment mode is planar. It may be covered in a simple manner by a simple, flat ceramic pane 8. This pane 8 is fitted with boreholes 9 through which the feed conductors 3 pass. The insulating sheath 4 terminates at the ceramic pane 8.

In the above shown design, the plasma is allowed to form only at the convex functional surface 6, that is, within a defined zone dedicated to surgery. All other areas of the vaporization electrode 1, and in particular the feed conductors 3, remain insulated and free of plasma formation.

The invention claimed is:

1. A surgical vaporization electrode for vaporizing tissue in the presence of an electrically conductive liquid, wherein:
the electrode comprises an electrode head having a functional surface and a back side;
the back side is connected at a minimum of one connection site to a feed conductor enclosed by an insulating sheath;
a ceramic covering is fitted onto the back side of the electrode head;
the ceramic covering encloses the connection site;
the functional surface, ceramic covering and insulating sheath are exposed to the electrically conductive liquid when the vaporization electrode is used to vaporize tissue;
the functional surface of the electrode head defines a convex surface;
the back side of the electrode head on which the connection site is configured is planar; and
the ceramic covering on the back side is a ceramic pane.

2. The vaporization electrode as claimed in claim 1, wherein the feed conductor passes through a borehole in the ceramic covering.

3. The vaporization electrode as claimed in claim 1 wherein the back side is connected to two feed conductors.

4. A surgical vaporization electrode for vaporizing tissue in the presence of an electrically conductive liquid, wherein:
the electrode comprises an electrode head having a functional surface and a back side;
the back side is connected at a minimum of one connection site to a feed conductor enclosed by an insulating sheath;
a ceramic covering is fitted onto the back side of the electrode head;
the ceramic covering encloses the connection site;
the functional surface, ceramic covering and insulating sheath are exposed to the electrically conductive liquid when the vaporization electrode is used to vaporize tissue; and
the feed conductor is perpendicular to the back side in its end portion at the connection site.

5. The vaporization electrode as claimed in claim 4, wherein the functional surface of the electrode head defines a convex surface.

6. The vaporization electrode as claimed in claim 4, wherein the back side of the electrode head on which the connection site is configured is planar, and the ceramic covering on the back side is a ceramic pane.

7. The vaporization electrode as claimed in claim 5, wherein the back side of the electrode head on which the connection site is configured is planar, and the ceramic covering on the back side is a ceramic pane.

8. The vaporization electrode as claimed in claim 4, wherein the feed conductor passes through a borehole in the ceramic covering.

9. The vaporization electrode as claimed in claim 4, wherein the back side is connected to two feed conductors.

10. A surgical vaporization electrode for vaporizing tissue in the presence of an electrically conductive liquid, wherein:
the electrode comprises an electrode head having a functional surface and a back side;
the back side is connected at a minimum of one connection site to a feed conductor enclosed by an insulating sheath;
a ceramic covering is fitted onto the back side of the electrode head;
the ceramic covering encloses the connection site;
the functional surface, ceramic covering and insulating sheath are exposed to the electrically conductive liquid when the vaporization electrode is used to vaporize tissue; and
the functional surface of the electrode head defines a convex surface.

11. The vaporization electrode as claimed in claim 10, wherein the feed conductor passes through a borehole in the ceramic covering.

12. The vaporization electrode as claimed in claim 10, wherein the back side is connected to two feed conductors.

13. A surgical vaporization electrode for vaporizing tissue in the presence of an electrically conductive liquid, wherein:
the electrode comprises an electrode head having a functional surface and a back side;
the back side is connected at a minimum of one connection site to a feed conductor enclosed by an insulating sheath;
a ceramic covering is fitted onto the back side of the electrode head;
the ceramic covering encloses the connection site;
the functional surface, ceramic covering and insulating sheath are exposed to the electrically conductive liquid when the vaporization electrode is used to vaporize tissue;
the back side of the electrode head on which the connection site is configured is planar; and
the ceramic covering on the back side is a ceramic pane.

14. The vaporization electrode as claimed in claim 13, wherein the feed conductor passes through a borehole in the ceramic covering.

15. The vaporization electrode as claimed in claim 13, wherein the back side is connected to two feed conductors.

* * * * *